US009052264B2

(12) United States Patent
Bendahan et al.

(10) Patent No.: US 9,052,264 B2
(45) Date of Patent: Jun. 9, 2015

(54) SCANNING SYSTEMS

(75) Inventors: Joseph Bendahan, San Jose, CA (US); Willem G. J. Langeveld, Menlo Park, CA (US)

(73) Assignee: Rapiscan Systems, Inc., Torrance, CA (US)

( * ) Notice: Subject to any disclaimer, the term of this patent is extended or adjusted under 35 U.S.C. 154(b) by 0 days.

(21) Appl. No.: 13/577,170

(22) Filed: Aug. 3, 2012

(65) Prior Publication Data

US 2014/0161225 A1    Jun. 12, 2014

Related U.S. Application Data

(63) Continuation of application No. PCT/IB2011/050469, filed on Feb. 3, 2011.

(30) Foreign Application Priority Data

Feb. 3, 2010    (GB) .................................. 1001738.2

(51) Int. Cl.
*G21K 1/00* (2006.01)
*G01N 23/04* (2006.01)
*G01V 5/00* (2006.01)

(52) U.S. Cl.
CPC .............. *G01N 23/04* (2013.01); *G01V 5/0016* (2013.01)

(58) Field of Classification Search
CPC ..................................................... G21K 1/043
USPC ................................................. 378/156–159
See application file for complete search history.

(56) References Cited

U.S. PATENT DOCUMENTS

| | | |
|---|---|---|
| 3,919,467 A | 11/1975 | Peugeot |
| 4,831,260 A | 5/1989 | DiBianca |
| 5,040,199 A | 8/1991 | Stein |
| 5,319,696 A | 6/1994 | Abdel-malek et al. |
| 5,321,271 A | 6/1994 | Schonberg et al. |
| 5,418,372 A | 5/1995 | Schonberg et al. |
| 5,661,377 A | 8/1997 | Mishin et al. |

(Continued)

FOREIGN PATENT DOCUMENTS

| | | |
|---|---|---|
| EP | 0417965 | 3/1991 |
| WO | WO0033060 | 6/2000 |

(Continued)

OTHER PUBLICATIONS

International Search Report for PCT/US09/47292, mailed on Apr. 23, 2012, Rapiscan Laboratories, Inc.

(Continued)

*Primary Examiner* — Hoon Song
(74) *Attorney, Agent, or Firm* — Novel IP

(57) ABSTRACT

A scanner system comprises: a radiation generator arranged to generate radiation to irradiate an object, the radiation generator comprising a radiation source arranged to produce radiation and a filter arranged to provide variable filtering of the radiation from the source; a detector structure arranged to detect the radiation after it has interacted with the object and generate a sequence of detector data sets as the object is moved relative to the generator, and a processing system arranged to process each of the detector data sets thereby to generate a control output arranged to control the radiation generator so as to vary the filtering, thereby to vary the radiation output by the radiation generator as the object is scanned.

8 Claims, 2 Drawing Sheets

(56) References Cited

U.S. PATENT DOCUMENTS

| | | |
|---|---|---|
| 5,838,759 A | 11/1998 | Armistead |
| 5,909,478 A | 6/1999 | Polichar et al. |
| 5,949,811 A | 9/1999 | Baba et al. |
| 5,974,111 A | 10/1999 | Krug et al. |
| 6,438,201 B1 | 8/2002 | Mazess et al. |
| 6,459,761 B1 | 10/2002 | Grodzins et al. |
| 6,713,773 B1 | 3/2004 | Lyons et al. |
| 6,847,040 B2 | 1/2005 | Strommer |
| 7,010,094 B2 | 3/2006 | Grodzins et al. |
| 7,272,208 B2 | 9/2007 | Yatsenko et al. |
| 7,369,642 B2 | 5/2008 | Eilbert et al. |
| 7,372,944 B2 | 5/2008 | Bernhardt et al. |
| 7,538,325 B2 | 5/2009 | Mishin et al. |
| 7,809,104 B2 | 10/2010 | Foland |
| 8,054,937 B2 | 11/2011 | Langeveld et al. |
| 8,437,448 B2 | 5/2013 | Langeveld et al. |
| 8,781,067 B2 | 7/2014 | Langeveld et al. |
| 2005/0117683 A1 | 6/2005 | Mishin et al. |
| 2005/0123101 A1* | 6/2005 | Akutsu et al. ............ 378/157 |
| 2007/0211851 A1* | 9/2007 | Ogawa ...................... 378/42 |
| 2008/0211431 A1 | 9/2008 | Mishin et al. |

FOREIGN PATENT DOCUMENTS

| | | |
|---|---|---|
| WO | WO0159485 | 8/2001 |
| WO | WO2006000020 | 1/2006 |
| WO | WO2006053279 | 5/2006 |
| WO | WO2009000020 | 12/2008 |
| WO | WO2009027667 | 3/2009 |
| WO | WO2009137698 | 12/2009 |
| WO | WO2010019311 | 2/2010 |
| WO | WO2011095810 | 8/2011 |

OTHER PUBLICATIONS

International Search Report for PCT/GB2011/050182, mailed on Dec. 28, 2011, Rapiscan Systems Inc.

* cited by examiner

SCANNING SYSTEMS

CROSS-REFERENCE

The present application is a continuation application, under 35 §365(c), of PCT/GB2011/050469, filed on Feb. 3, 2011, which relies on Great Britain Patent Application No. 1001738.2, filed on Feb. 3, 2010. All of the aforementioned applications are herein incorporated by reference.

FIELD

The present application relates to scanning systems, in particular security scanning systems, and has particular application in the use of high energy X-radiation to inspect packages, cargo, containerised loads and vehicles for the presence of illicit materials and devices.

BACKGROUND

X-ray radiography imaging of cargo containers and trucks for the detection of nuclear material and other contraband requires high-intensity X-ray radiation sources. The higher the source intensity at a specific source energy, the greater the amount of material the X-ray beam can penetrate and the better the contrast resolution. In current practice, the X-ray source intensity of an inspection system is typically set to the highest level allowable (referred to herein as the Output Set Point or OSP) under the particular circumstances of the system and the inspection area, and all cargo is inspected using this fixed intensity, whether the accurate inspection of the cargo requires this intensity or not. This OSP is, however, typically not the highest rated intensity that the source is capable of producing. More often than not, the OSP is set to not exceed a specified radiation dose limit at the boundary of a predefined exclusion zone, or, in case of a portal inspection system (where truck drivers drive their trucks through the inspection system), to stay below a certain dose limit to the driver of the inspected truck. There are, therefore, two deficiencies of the current practice:
1. The rated maximum intensity of the source is usually higher than the OSP and the inspection system is therefore intrinsically capable of providing higher cargo penetration than it is set to provide;
2. The system uses much higher intensity for certain cargos (or parts thereof) than needed, leading, on average, to unnecessarily high radiation levels around the inspection system.

SUMMARY

The present application discloses a scanner system. The scanner system may comprise a radiation generator arranged to generate radiation to irradiate an object. The radiation generator may comprise a radiation source arranged to produce radiation and a filter arranged to provide variable filtering of the radiation from the source. The system may further comprise detection means, for example a detection system, arranged to detect the radiation after it has interacted with the object, and which may generate a sequence of detector data sets as the object is moved relative to the generator. It may further comprise processing means, for example at least one processor, arranged to process each of the detector data sets thereby to generate a control output arranged to control the radiation generator, for example so as to vary the filtering, thereby to vary the radiation output by the radiation generator as the object is scanned.

The processing means may be arranged to define a parameter of the detector data, to determine a value of the parameter for each data set, and generate a control output arranged to vary the radiation output depending on the value, for example if the value of the parameter does not meet a predetermined condition.

The detection means may comprise a plurality of detectors. The detector data may comprise a set of intensity values indicative of the intensity of radiation at each of the detectors.

The filter may comprise a filter element, which may be movable between a plurality of positions so as to provide a plurality of different levels of filtering.

The filter may comprise a plurality of filter sections and may be arranged to move so that each of the filter sections is aligned with the radiation in turn.

Indeed the present invention further provides a scanner system comprising a radiation source arranged to produce radiation, detection means arranged to detect the radiation after it has interacted with an object thereby to produce data sets, a filter comprising a plurality of filter sections and arranged to move so that each of the filter sections is aligned with the radiation in turn, and a processing system arranged to control at least one of the filter, the source, and the detection means thereby to control the level of filtering of the detected radiation.

The radiation generator may be arranged to generate the radiation in pulses, and may, for example under the control of the processing system, be arranged to vary the timing of the pulses so as to vary which of the filter sections is aligned with the radiation when the data sets are collected.

The processing system may be arranged to vary the timing of collection of the data sets, thereby to vary which of the filter sections is aligned with the radiation when the data sets are collected.

The filter sections may have different filter characteristics. For example they may be of different thicknesses, and they may be made of the same material, or they may be made of different materials.

The filter may be rotatable, or it may be movable linearly, or in a reciprocating manner.

Preferred embodiments of the present invention will now be described by way of example only with reference to the accompanying drawings.

DETAILED DESCRIPTION

Figure 1:
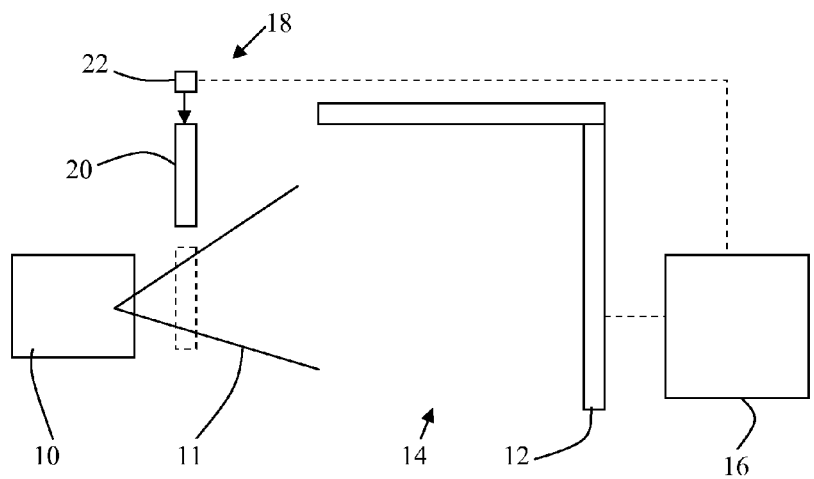
FIG. 1 is a schematic view of a radiation imaging system according to an embodiment of the invention.

Referring to FIG. 1, an X-ray imaging system comprises an X-ray generator 10 arranged to generate a beam 11 of X-rays, and a detector array 12 arranged to detect the X-rays after they have passed through an imaging volume 14. The X-ray generator is arranged to produce the beam in the form of a vertically extending fan beam, and the detector array 12 comprises a vertical linear detector array 12a and a horizontal linear detector array 12b. Therefore the imaging volume 14 is in the form of a thin vertical slice. A processing system 16 is arranged to receive detector signals from each of the detectors in the detector array 12 and to process the detector signals so as to generate image data. A variable filter system 18 comprises a filter element 20, which in this case is formed of sheet metal, and is movably mounted so that it can move between a deployed position in which it is placed in the path of the X-ray beam 11, and a retracted position in which it is not in the path of the X-ray beam. An actuator 22 is connected to the filter element 20 and is arranged to move the filter element 20 between its deployed and retracted positions. The processing system 16 is arranged to analyse the detectors signals and control the actuator 22 to control the position of the filter element in response to that analysis.

In operation, the system starts with the filter element in its deployed position, and the source 10 is arranged to generate X-rays in pulses, and for each pulse the processing system 16 is arranged to sample the detector signals to generate an image data set, from which a two-dimensional image can be generated. The image data set in this case comprises a set of intensity values, one for each detector in the array 12. As the object moves through the imaging volume, in the direction into or out of the page of FIG. 1, a series of data sets is collected which can then be built up to form a 2D image of the object. As each data set is collected, the processing system 16 is arranged to analyse it to determine whether it meets a condition, which in this case is that all of the detectors in the detector array 12 receive at least a minimum level of radiation. If this condition is met, then the processing system simply waits for the next radiation pulse so that it can collect the next set of data. However, if the condition is not met, the processing system sends a signal to the actuator 22 which is arranged to respond by moving the filter element to its retracted position. This reduces the amount of radiation that the filter blocks, and therefore increases the intensity or the X-ray beam 11, which in turn increases the level of radiation detected by the detector array 12. The filter is maintained in the retracted position until a further condition is met, which in this case is that all of the detectors detect a second level of radiation, which is higher than the minimum level. If this condition is met, then the processing system is arranged to control the actuator to move the filter element back to the deployed position. The gap between the higher and lower set levels provides a degree of hysteresis around the switch point.

Figure 2:
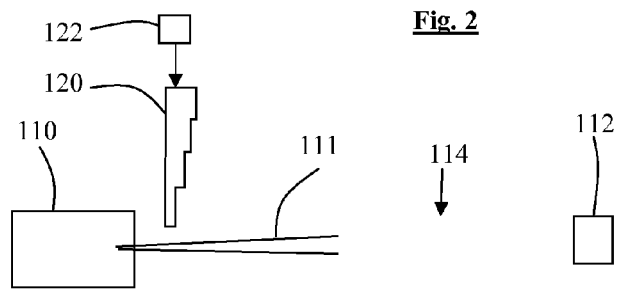
FIG. 2 is a schematic view of a radiation imaging system according to a further embodiment of the invention.

Referring to FIG. 2, in a second embodiment of the invention, which is similar to the first embodiment, but here shown in plan view, the filter element 120 is of varying thickness, having a number of sections 120a, 120b, 120c, 120d of different thicknesses. In this case the filter element is located to the side of the X-ray fan beam 111 so that the distance that it needs to move is minimized. In this embodiment the filter element has five positions, corresponding to each of the four sections 120a, 120b, 120c, 120d being in line with the X-ray beam 111, and the filter element 120 being completely clear of the X-ray beam a shown in FIG. 2. In this case, the processing system (not shown) is arranged to analyse each set of image data, which again relates to a 2D image slice, and select the appropriate position for the filter element 120 for the subsequent slice image. It is then arranged to send a signal to the actuator 122 to move the filter element 120 to the required position. As with the first embodiment, the conditions which have to be met for the filter element to be moved can be defined in a number of ways.

Figure 3:
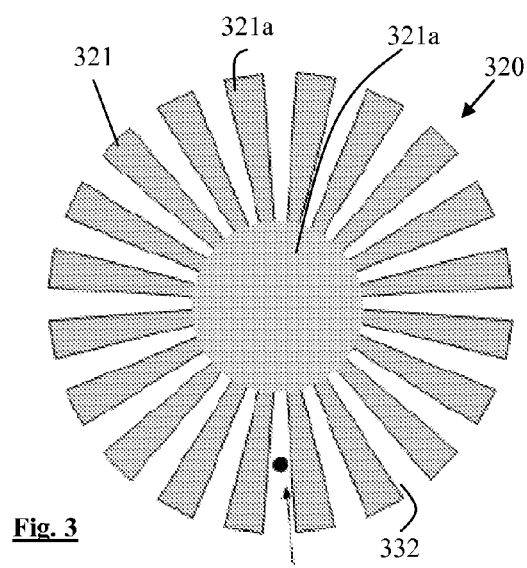
FIG. 3 is a front view of a filter wheel forming part of a radiation imaging system according to a further embodiment of the invention.
Figure 4:
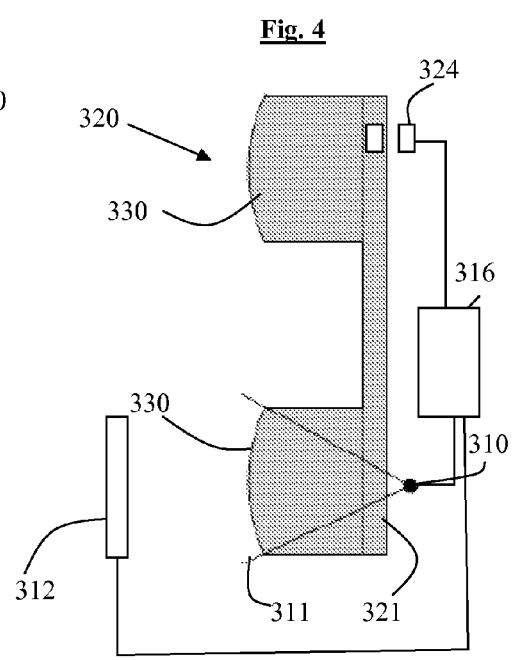
FIG. 4 is a section through the filter wheel of FIG. 2.
Figure 5:
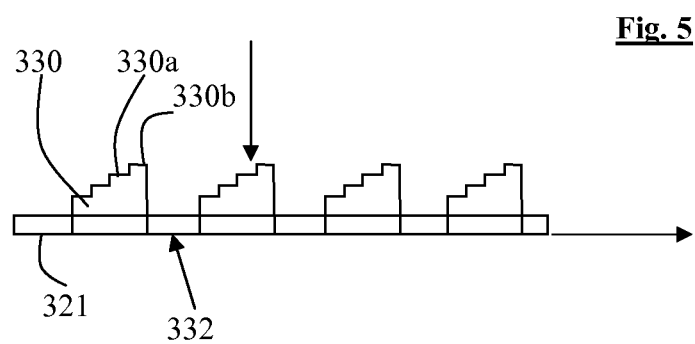
FIG. 5 is a further section through the filter wheel of FIG. 2.

Referring to FIGS. 3 and 4, a scanner system according to a third embodiment is similar to that of FIG. 2, except that the filter 320 comprises a filter wheel comprising a rotatable plate 321 arranged to rotate about an axis parallel to the centre line of the X-ray beam 311, with a number of filter blocks 330 formed on it, and evenly spaced around its axis of rotation. The plate 321 comprises a central portion 321a, with a number of spokes or blades 321b extending radially outwards from the central portion, and having gaps 332 between them. Each of the filter blocks 330 is mounted on a respective one of the spokes 321b. Referring to FIG. 5, which is a section along an arc of the filter wheel 320, each of the filter blocks 330 is made up of a number of sections 330a, 330b, side by side in the circumferential direction and each extending across the full width of the filter block 330 in the radial direction, which are of different thicknesses. In this embodiment there are 20 spokes of the wheel and 20 filter blocks 320. The filter 320 is located so that, as the plate 321 rotates about its axis, each of the filter sections 330a, 330b of each of the filter blocks 330, alternating with the gaps 332 between the filter blocks, is placed in turn in the path of the X-ray beam 311, between the X-ray source 310 and the detector array 312, so that it filters the X-ray beam 311. The processing system 316 is arranged to receive the detector signals from the detector array 312, and also to receive signals from a rotary position sensor 324 which is arranged to detect the rotary position of the filter wheel 320. From the position signal, the processing system 316 can determine which of the filter sections 330a, 330b is in the path of the X-ray beam at any time. The processing system 316 is also arranged to control operation of the X-ray source 310 so as to produce X-rays in pulses, and the timing of the pulses can be controlled by the processing system. The pulses are produced at the frequency of the rotation of the filter wheel 320 multiplied by the number of filter blocks 330, which in this case is twenty. Therefore twenty pulses (one for each filter block) can be transmitted during each rotation of the filter wheel 320, each coinciding with a respective one of the filter sections 330a, 330b, or gap 332, being aligned with the X-ray beam 311.

The processing system is arranged to add or remove a delay into the pulse train to shift the pulse timings so as to coincide with alignment of a different set of filter block sections 330a, 330b, or the gaps 332, thereby to vary the degree of filtering of the X-ray pulses.

Operation of this system is similar to those described above in that the after each data set is collected, typically comprising a single sample from each detector in the linear array 312, the processing system analyses the detector signals to check for the meeting of one or more conditions, and then determines whether the degree of filtering needs to be increased or decreased for the next or another subsequent data set. If it does, then the processing system is arranged to shift the timings of the X-ray pulses by a timing offset equal to the filter section transition period to the desired filter section, i.e. the time between alignment of subsequent filter sections with the X-ray beam, thereby to select a different set of operative filter sections of the required thickness. Depending on the type of detector used, the processing system 316 may also be arranged to shift the detector signal sampling times so that they remain synchronized with the X-ray pulses. The degree of filtering, and hence the intensity of the X-ray beam reaching the object, can therefore be adjusted after each detector data set is collected.

Figure 6:
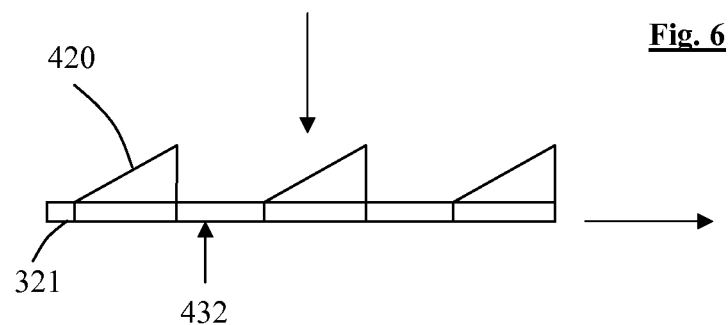
FIG. 6 is a section similar to FIG. 5 through a filter wheel according to a further embodiment of the invention.

Referring to FIG. 6, in a modification to the embodiment of FIG. 5, each stepped filter block 320 is replaced by a filter block 420 of continuously varying thickness, the thickness varying in the circumferential direction of the filter wheel. The timing of the X-ray pulses is therefore controlled to determine which part of the filter block 320 they pass through, which determines how much filtering they experience.

In a further modification to the embodiments of FIGS. 5 and 6, the processing system 322 is arranged to control the speed of the motor driving the filter wheel, which enables it to select different thickness filter sections to be the operative filter sections by varying the speed of the filter wheel, while the X-ray pulse frequency remains fixed.

We claim:

1. A scanner system comprising:
   a radiation generator arranged to generate radiation to irradiate an object, the radiation generator comprising a radiation source arranged to produce pulses of an X-ray beam and a filter arranged to provide variable filtering of the X-ray beam from the source, wherein said filter comprises a rotatable plate having a plurality of spokes extending radially from a center of said rotatable plate and arranged to rotate about an axis parallel to a center line of the X-ray beam, wherein each of said plurality of spokes is separated by a gap, and wherein each of said spokes comprises a filtering block having a plurality of sections with different filtering characteristics;
   a detector structure arranged to detect the X-ray beam after said X-ray beam has interacted with the object and generate a sequence of detector data sets as the object is moved relative to the generator, and
   a processor system to process each of the detector data sets and to generate a control output, wherein the processor system uses the control output to modify a timing of said pulses of the X-ray beam so as to coincide with different sections of the plurality of sections, thereby providing said variable filtering and varying a radiation output by the radiation generator as the object is scanned.

2. A scanner system according to claim 1 wherein the processor system is arranged to define a parameter of the detector data, to determine a value of the parameter for each data set, and generate a control output arranged to vary the radiation output if the value of the parameter does not meet a predetermined condition.

3. A scanner system according to claim 1 wherein the detector structure comprises a plurality of detectors and the detector data comprises a set of intensity values indicative of the intensity of radiation at each of the detectors.

4. A scanner system according to claim 1 wherein the filter comprises a filter element movable between a plurality of positions so as to provide a plurality of different levels of filtering.

5. A scanner system comprising
   a radiation source arranged to produce a pulse train of X-ray radiation,
   a detector structure arranged to detect the X-ray radiation after it has interacted with an object thereby to produce data sets,
   a filter comprising a plurality of filter sections, wherein said filter comprises a rotatable plate having a plurality of spokes extending radially from a center of said rotatable plate and arranged to rotate about an axis parallel to a center line of the X-ray beam, wherein each of said plurality of spokes is separated by a gap, wherein each of said spokes comprises a filtering block having said plurality of filter sections with different filtering characteristics and wherein said filter is arranged to rotate so that each of the plurality of filter sections is aligned with a pulse of the X-ray radiation in turn; and
   a processing system arranged to control at least one of the plurality of filter sections to control the level of filtering of the detected radiation, wherein said processing system uses the data sets to determine whether to rotate at least one of the plurality of filter sections in order to vary a X-ray radiation output by the radiation generator as the object is scanned and wherein the processing system causes said plurality of filter sections to rotate based on said determination.

6. A scanner system according to claim 5 wherein the processing system is arranged to vary the timing of the pulses so as to vary which of the plurality of filter sections is aligned with the X-ray radiation when the data sets are collected.

7. A scanner system according to claim 6 wherein the processing system is arranged to vary a timing of a collection of the data sets, so that they remain synchronized with the X-ray radiation pulses.

8. A scanner system according to claim 5 wherein each of the plurality of filter sections have different thicknesses.

* * * * *